US011510410B2

(12) United States Patent
Harding et al.

(10) Patent No.: US 11,510,410 B2
(45) Date of Patent: *Nov. 29, 2022

(54) PEDICULICIDAL COMPOSITION

(71) Applicant: DR. REDDY'S LABORATORIES, S.A., Basel (CH)

(72) Inventors: Ronald Harding, Warrandyte (AU); Lewis David Schulz, Fitzroy North (AU); Vernon Morrison Bowles, Glen Iris (AU)

(73) Assignee: Hatchtech Pty Limited

(*) Notice: Subject to any disclaimer, the term of this patent is extended or adjusted under 35 U.S.C. 154(b) by 168 days.

This patent is subject to a terminal disclaimer.

(21) Appl. No.: 16/366,573

(22) Filed: Mar. 27, 2019

(65) Prior Publication Data

US 2019/0216086 A1  Jul. 18, 2019

Related U.S. Application Data

(63) Continuation of application No. 14/573,079, filed on Dec. 17, 2014, now Pat. No. 10,292,389.

(60) Provisional application No. 61/917,078, filed on Dec. 17, 2013.

(51) Int. Cl.
*A01N 43/40* (2006.01)
*A01N 25/30* (2006.01)

(52) U.S. Cl.
CPC ............ *A01N 43/40* (2013.01); *A01N 25/30* (2013.01)

(58) Field of Classification Search
CPC ................................. A01N 43/40; A01N 25/30
See application file for complete search history.

(56) References Cited

U.S. PATENT DOCUMENTS

| | | | |
|---|---|---|---|
| 4,177,349 A | 12/1979 | McGill | |
| 4,357,329 A | 11/1982 | Heywang et al. | |
| 4,690,818 A | 9/1987 | Puchalski | |
| 4,853,396 A | 8/1989 | Farooq | |
| 5,100,436 A | 3/1992 | Wenke | |
| 5,112,515 A | 5/1992 | Buxton | |
| 5,200,427 A | 4/1993 | Rebelz et al. | |
| 5,288,483 A | 2/1994 | Cardin et al. | |
| 5,608,059 A | 4/1997 | Wear | |
| 5,717,060 A | 2/1998 | Sommazzi et al. | |
| 5,731,303 A | 3/1998 | Hsieh | |
| 5,766,609 A | 6/1998 | Grieve et al. | |
| 5,985,273 A | 11/1999 | Reed et al. | |
| 6,150,125 A | 11/2000 | Grieve et al. | |
| 6,180,084 B1 | 1/2001 | Ruoslahti et al. | |
| 6,426,093 B1 | 7/2002 | Chevion et al. | |
| 6,607,716 B1 | 8/2003 | Smith et al. | |
| 6,663,876 B2 | 12/2003 | Campbell et al. | |
| 6,668,876 B2 | 12/2003 | Veinotte et al. | |
| 6,727,228 B2 | 4/2004 | Janssen et al. | |
| 7,294,342 B2 * | 11/2007 | Precopio | A01N 31/04 424/407 |
| 7,812,163 B2 | 10/2010 | Bowles | |
| 8,212,038 B2 | 7/2012 | Bowles | |
| 9,357,783 B2 * | 6/2016 | Bowles | A01N 37/46 |
| 10,292,389 B2 * | 5/2019 | Harding | A01N 25/30 |
| 2001/0044470 A1 | 11/2001 | Sembo et al. | |
| 2002/0032339 A1 | 3/2002 | Marcuccio | |
| 2003/0060471 A1 | 3/2003 | Okui et al. | |
| 2004/0062785 A1 * | 4/2004 | Parker | A01N 25/006 424/410 |
| 2005/0008714 A1 | 1/2005 | Enan | |
| 2006/0140995 A1 | 6/2006 | Precopio | |
| 2006/0178404 A1 | 8/2006 | Bowles | |
| 2007/0254907 A1 | 11/2007 | Bowles | |
| 2009/0143419 A1 | 6/2009 | Bowles | |
| 2013/0005765 A1 | 1/2013 | Bowles | |

FOREIGN PATENT DOCUMENTS

| | | |
|---|---|---|
| AU | 466 960 | 10/1973 |
| BR | 9508041 A | 11/1997 |
| CA | 2 394 002 A1 | 6/2001 |
| CA | 2 408 209 A1 | 11/2002 |
| CN | 1074900 A | 8/1993 |
| CN | 101686678 A | 3/2010 |
| EP | 0 191 236 A1 | 8/1986 |
| EP | 0 603 696 A1 | 6/1994 |
| EP | 0797996 | 1/1997 |
| JP | 9506865 | 7/1997 |
| JP | 10-504278 | 4/1998 |
| JP | 10-507455 | 7/1998 |

(Continued)

OTHER PUBLICATIONS

Shionogi et al. (Ulefsia product page, published 2009 (Year: 2009).*
Carbomer. Medical Dictionary. Published 2022 (Year: 2022).*
Ferris, H., "The role of nematodes in soil fertility," Department of Nematology, University of California, Davis, California, 2 pages (1998).
Al-Sayah et al., "Structural Studies on Hydrogen-Bonding Receptors for Barbiturate Guests That Use Metal Ions as Allosteric Inhibitors," Eur. J. Org. Chem., 173-182 (2004).
Buhleier et al., "2,2'-Bipyridine as a Building Block for New Aza Crown Ethers and Cryptands," Chem. Bur., 111:200-204 (1978).
Busvine, "Malaria transmission—mosquitoes, humans and their behaviour," Antenna, 18(1):18-22 (1997).

(Continued)

*Primary Examiner* — Theodore R. Howell
*Assistant Examiner* — George W Kosturko
(74) *Attorney, Agent, or Firm* — McAndrews, Held & Malloy, Ltd.

(57) ABSTRACT

The disclosure provides a pediculicidal composition comprising a metal chelating agent; a carrier vehicle comprising water and an activating solvent system comprising an alcohol and a hydrocarbon. The carrier vehicle may be in the form of a solution, a cream, an ointment, a foam, a spray, an emulsion or a gel. The disclosure also provides method for use of a pediculicidal composition to treat human head lice and their eggs and methods for controlling head lice infestation.

13 Claims, No Drawings

(56) References Cited

FOREIGN PATENT DOCUMENTS

| | | | |
|---|---|---|---|
| JP | 11-222429 | 8/1999 | |
| JP | 2002363008 | 12/2002 | |
| JP | 2008007444 | 1/2008 | |
| JP | 2010511723 | 4/2010 | |
| JP | 2012102033 | 5/2012 | |
| RU | 2205626 C1 * | 6/2003 | |
| WO | 89/10693 A1 | 11/1989 | |
| WO | 9510999 | 4/1995 | |
| WO | 96/11706 A1 | 10/1995 | |
| WO | 95/35031 A1 | 12/1995 | |
| WO | 2005/007188 A1 | 1/2005 | |
| WO | 2006/076761 A1 | 7/2006 | |
| WO | WO-2006076761 A1 * | 7/2006 | ............ A01N 61/00 |
| WO | 2008020602 | 6/2008 | |
| WO | WO-2009047584 A1 * | 4/2009 | ............ A01N 61/00 |
| WO | WO-2012096386 A1 * | 7/2012 | ......... B01J 35/1009 |
| WO | WO-2012096836 A1 * | 7/2012 | ................ C10L 1/23 |

OTHER PUBLICATIONS

Imperiali et al., "Stereoselective Synthesis and Peptide Incorporation of (S)-a-Amino-(2,2'-bipyridine)-6-propanoic Acid," J. Org. Chem., 57:757-759 (1992).

Case, "The Synthesis of Certain Substituted 2,2'-Biyridyls," Journal of American Chemical Society, 68:2574-2577 (1946).

"Final Report on the Safety Assessment of EDTA, Calcium Disodium EDTA, Diammonium EDTA, Dipotassium EDTA, Disodium EDTA, TEA-EDTA, Tetrasodium EDTA, Tripotassium EDTA, Trisodium EDTA, HEDTA, and Trisodium HEDTA," International Journal of Toxicology, 21(Suppl.2):95-142 (2002).

Database WPI Week 200342, Thomson Scientific, 2 pages, XP002548581.

Dymock et al., "Behavioural and physiological responses of grass grub larvae (*Costelytra zealandica*) feeding on protease inhibitors," New Zealand Journal of Zoology, 19:123-131 (1992).

Young et al., "Characterisation of proteases involved in egg hatching of the sheep blowfly, *Lucilia cuprina*," International Journal of Parasitology, 30:925-932 (2000).

Reed et al., "Aminopeptidases as potential targets for the control of the Australian sheep blowfly, *Lucilia cuprina*," International Journal for Parasitology, 29:839-850 (1999), XP-002548584.

Samuels et al., "Cuticle degrading proteases from insect moulting fluid and culture filtrates of entomopathogenic fungi," Comp. Biochem. Physiol., 110B(4):661-669 (1995).

Suzuki et al., "Neutral endopeptidase modulates VIP-inducted vasodilation in hamster cheek pouch vessels in situ," American Journal of Physiology, 1 page (1996), XP-002548582.

Vieira et al., "Pro- and anti-inflammatory actions of ricinoleic acid: similarities and differences with capsaicin," Naunyn-Schmiedeberg's Arch Pharmacol, 364:87-95 (2001), XP-002548583.

Sochova et al., "Effects of seven organic pollutants on soil nematode Caenorhabditis elegans," Environment International, 33:798-804 (2007).

Averina et al, "Controlling rose aphids with o-phenanthroline," HCA, 110:19870, Abstract.

International Search Report for Application No. PCT/IB2007/003226 dated Nov. 4, 2008.

Extended European Search Report for Application No. EP 07 82 5504 dated May 4, 2011.

International Preliminary Report on Patentability for Application No. PCT/AU2006/000028 dated Jul. 24, 2007.

International Preliminary Report on Patentability for Application No. PCT/IB2007/003226 dated Oct. 6, 2009.

Examination Report issued in New Zealand Application No. 580312 dated Apr. 10, 2012, 2 pages.

Notice of Publication of Application of Patent for Invention. Application No. 200780053181.2. dated May 6, 2010 (published specification attached hereto), 109 pages.

Notice of Preliminary Examination on the Patent Application for Invention, Application No. 200780053181.2, dated May 6, 2010, 1 page.

European Search Report corresponding to European Patent Application No. 04737575.3-1223, dated Oct. 29, 2009, 8 pages.

International Preliminary Report on Patentability for Application No. PCT/AU2004/000955 dated Jan. 16, 2006, 4 pages.

International Search Report and Written Opinion in PCT/AU2006/000028, dated Feb. 16, 2006, 12 pages.

Pearlman, "A Sipple Treatment for Head Lice: Dry-On, Suffocation-Based Pediculicide", Pediatrics vol. 114, No. 3, Sep. 3, 2004, 8 pages.

Ulesfia-benzyl alcohol lotion product page. Shionogi Inc., (Year: 2009).

Hipolito et al (Pediatrics vol. 107 e30 pp. 1-5 published 2001).

* cited by examiner

PEDICULICIDAL COMPOSITION

CROSS REFERENCE TO RELATED APPLICATIONS

The present application is a continuation of U.S. Non-Provisional patent application Ser. No. 14/573,079, filed Dec. 17, 2014, which claims the benefit of priority to U.S. Provisional Patent Application Ser. No. 61/917,078, filed Dec. 17, 2013. The entire text of the aforementioned applications is incorporated herein by reference in its entirety.

FIELD

The present invention relates to compositions and methods for treating human head lice, *Pediculus humanus capitis*. In particular, the invention relates to a pediculicidal composition and the methods of use.

BACKGROUND

Head lice persist in developed and underdeveloped countries despite the availability of modern chemical insecticide treatments, public health education, and community based programs of lice eradication. The persistence of head lice is due to a combination of factors. Some lice control programs suffer logistical problems. Additionally, while shampoo formulations continue to retain widespread popularity, some chemical treatments are not entirely effective.

Various compositions and methods have been used to treat a head lice infestation. For example, lice and their eggs are mechanically removed with combs and killed with insecticides (known as pediculicides). Pediculicides, or pediculicidal compositions, are used to treat lice infestations and hence typically display both lousicidal and ovicidal activity. For example, lindane and various pyrethroids, have been used in conjunction with shampoos for treating head lice infestations. However, the use of these compositions and methods is not entirely effective in controlling head lice because some lice or their eggs (nits) often survive the treatment. Lice have also begun to develop resistance to current pediculicides and thus a new compound for killing lice and their eggs is desirable.

Accordingly, there remains a need for pediculicidal compositions that are easy to use and are highly effective against lice and their eggs. The present invention addresses these unmet needs.

SUMMARY

The disclosure relates to compositions and methods for treating human head lice, *Pediculus humanus capitis*. In particular, the disclosure is directed to pediculicidal compositions and methods of use, as well as to uses of the compositions for treating infestation on a host. In an embodiment, the pediculicidal composition comprises: a metal chelating agent, an oil phase comprising an activating solvent system, and an aqueous phase which combines with the oil phase to form a carrier vehicle. More specific embodiments relate to compositions comprising 5,5'-dimethyl-2,2'-dipyridyl; an oil phase comprising an activating solvent system that comprising an alcohol and a hydrocarbon; and an aqueous phase which combines with the oil phase to form a carrier vehicle.

In an aspect, the disclosure provides a composition comprising 5,5'-dimethyl-2,2'-dipyridyl; a carrier vehicle comprising an activating solvent system comprising an alcohol and a hydrocarbon; and an aqueous phase which combines to form the carrier vehicle; wherein 5,5'-dimethyl-2,2'-dipyridyl is present in the composition at a concentration from about 0.25% by weight or greater wherein said composition exhibits both ovicidal and lousicidal activity. In some embodiments the alcohol comprises an aromatic or aryl alcohol such as, for example benzyl alcohol or phenoxyethanol. In some embodiments the hydrocarbon comprises mineral oil. In further embodiments, the composition may comprise 5,5'-dimethyl-2,2'-dipyridyl at a concentration from about 0.25% to about 5% by weight, or from about 0.5% to about 5% by weight, or from about 0.25% to about 1%, or from about 0.5% to about 1% by weight. In some embodiments the carrier vehicle in the composition can be formulated as a solution, a gel, a cream, an ointment, a foam, a spray or an emulsion. In some embodiments, the carrier vehicle may comprise water, the activating solvent system, and at least one agent selected from the group consisting of a thickening agent, a pH adjuster, one or more surfactant, emulsifying agents, and an anti-oxidant. In some embodiments, the thickening agent is selected from the group consisting of acritamers, carbomers or pemulens. In some embodiments the thickening agent comprises a carbomer. More than one thickening agent can be used. In some embodiments the pH adjuster comprises a base such as, for example, trolamine (also known as triethanolamine). More than one pH adjuster can be used. In some embodiments the surfactant may be selected from a polysorbate (e.g., polysorbate 20). In some embodiments the surfactant may also act as an emulsifying agent, and more than one emulsifying agent may also be used. In some embodiments, the anti-oxidant is butylated hydroxytoluene (BHT). More than one anti-oxidant can be used. In some embodiments, the pH adjuster may also have surfactant properties such as, for example, triethanolamine.

In another aspect, the disclosure relates to a composition comprising 5,5'-dimethyl-2,2'-dipyridyl in an amount from about 0.25% to about 5% by weight; benzyl alcohol in an amount from about 0.5% to about 10% by weight; mineral oil in an amount from about 2% to about 35% by weight; water in an amount from about 35% to about 95% by weight; carbomer in an amount from about 0.1% to about 1% by weight; trolamine in an amount from about 0.1% to about 2% by weight; and polysorbate 20 in an amount from about 0.1% to about 5% by weight. In some embodiments of this aspect the 5,5'-dimethyl-2,2'-dipyridyl may be present in an amount from about 0.5% to about 1% by weight; the benzyl alcohol may be present in an amount from about 1% to about 3% by weight; the mineral oil may be present in an amount from about 20% to about 30% by weight; the water may be present in an amount from about 60% to about 90% by weight; the carbomer may be present in an amount from about 0.1% to about 0.5% by weight; the trolamine may be present in an amount from about 0.1% to about 1% by weight; and the polysorbate 20 may be present in an amount from about 0.5% to about 2% by weight.

In further embodiments of this aspect, the composition can be formulated as a lotion, a cream, an emulsion, a foam or a gel and may comprise about 0.74% by weight 5,5'-dimethyl-2,2'-dipyridyl; and/or about 24% by weight mineral oil; and/or about 1% by weight polysorbate 20; and/or about 2% by weight benzyl alcohol.

In some embodiments the composition comprises 2% by weight benzyl alcohol, 24% mineral oil, 1% polysorbate 20 and 0.74%, 5,5'-dimethyl-2,2'-dipyridyl and said composition exhibits a greater lousicidal activity than a similar composition that does not comprise 5,5'-dimethyl 2,2'-dipyridyl.

In further embodiments the composition comprises 2% by weight benzyl alcohol, 24% mineral oil, 1% polysorbate 20 and 0.74%, 5,5'-dimethyl-2,2'-dipyridyl and said composition exhibits a greater ovicidal activity than a similar composition that does not comprise 5,5'-dimethyl 2,2'-dipyridyl.

In another aspect, the disclosure provides an aqueous composition for topical application to a subject comprising by weight: 0.74% 5,5'-dimethyl-2,2'-dipyridyl; 24% mineral oil; 2.00% benzyl alcohol, 0.15% Carbomer; 0.2% Trolamine; 1% polysorbate 20, 0.5% BHT and the balance purified water.

In a further aspect the disclosure relates to a method of treating a lice infestation, the method comprising topically applying to a host having a lice infestation an effective amount of a composition according to the various aspects and embodiments described herein. In embodiments, the method may kill lice and inhibit lice eggs from hatching. In further embodiments, the method may kill more lice and inhibit eggs from hatching relative to a vehicle composition comprising the same components except for 5,5'-dimethyl-2,2'-dipyridyl.

Other embodiments of the invention provide methods of treating pest infestation comprising administering to a subject in need thereof, a therapeutically effective amount of the pediculicidal compositions disclosed herein.

The disclosure provides for other aspects and embodiments that will be apparent in view of the description that follows.

DETAILED DESCRIPTION

In an aspect, the invention provides a pediculicidal composition formulation. The pediculicidal composition comprises a metal chelating agent, an activating solvent system, and a carrier vehicle. In a specific embodiment, the pediculicidal composition comprises 5,5'-dimethyl-2,2'-dipyridyl, an oil phase comprising an activating solvent system, and an aqueous phase which combines with the oil phase to form a carrier vehicle. The inventors have identified that an activating solvent system can provide for increases in the pediculicidal activity of the compositions disclosed herein. Further, the inventors have identified the amount of surfactant included in the compositions can have an unexpected effect on the pediculicidal activity of the compositions disclosed herein.

The term "pediculicidal composition" is used herein to refer to a composition with a metal chelating agent that exhibits ovicidal and lousicidal activity against lice eggs and lice, respectively.

One of skill in the art will appreciate that any of the recited numeric ranges referred to herein (e.g., weight percent ranges) regarding any of the components of the compositions can encompass all weight percent values falling within those ranges (e.g., "about 1% to about 10%" includes about 1%, 2%, 3%, 4%, 5%, 6%, 7%, 8%, 9%, and 10% as well as including fractions of those weight percent values (e.g., 5.1%, 5.2%, 5.3%, 5.4%, 5.5%, 5.6%, 5.7%, 5.8%, and 5.9%) as well as sub-ranges within the broader range (e.g., "about 1% to about 10%" includes about 2% to about 8%, about 3% to about 6%, and about 6% to about 10%). These are just examples of the ranges and values falling within the scope of the identified ranges in the disclosure.

The term "metal chelating agent" as used herein refers to a compound comprising at least two heteroatoms able to simultaneously coordinate with a metal ion, at least one of the two heteroatoms being selected from nitrogen, sulphur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom.

Preferred metal chelating agents include, but are not limited to: 6,6'-dimethyl-2,2'-dipyridyl, 5,5'-dimethyl-2,2'-dipyridyl, 4,4'-dimethyl-2,2'-dipyridyl or a pharmaceutically, veterinary or agriculturally acceptable salt thereof, preferably 5,5'-dimethyl-2,2'-dipyridyl.

In some embodiments, the pediculicidal composition comprises a metal chelating agent at a concentration preferably from about 0.25% or greater, preferably between from about 0.25% to about 5% by weight, more preferably between from about 0.25% to about 1% by weight. Specifically, a preferred composition comprises at least 0.25% or greater concentration of 5,5'-dimethyl-2,2'-dipyridyl. In some embodiments the composition comprises about 5%, 4.75%, 4.50%, 4.25%, 4.0%, 3.75%, 3.50%, 3.25%, 3.0%, 2.75%, 2.50%, 2.25%, 2.0%, 1.75%, 1.50%, 1.25%, 1.0%, 0.75%, 0.50%, or about 0.25% concentration of 5,5'-dimethyl-2,2'-dipyridyl. In specific embodiments, this component is present in a concentration of approximately 0.37% to about 0.9%, which range is inclusive of illustrative embodiments as described in the Examples (e.g., about 0.9%, 0.74%, 0.55%, 0.54%, 0.38%, and 0.37%).

The term "activating solvent system" as used herein refers to a mixture having at least a solvent and a co-solvent. As described herein, and as illustrated in the Examples, some embodiments of the disclosure provide an activating solvent system that provides for superior enhancement of the lousicidal and ovicidal activity of 5,5'-dimethyl-2,2'-dipyridyl in a pediculicidal composition. It is of note that the pediculicidal composition is one that exhibits both ovicidal and lousicidal activity. In some embodiments, an activating solvent system comprising an alcohol and a hydrocarbon provides for a composition that possesses unexpected ovicidal, lousicidal, and/or pediculicidal activity, as compared to similar compositions that lack one or more features of the activating solvent system. For example, an activating solvent system that preserves both the alcohol and the hydrocarbon combines to produce the unexpected and beneficial improvements in ovicidal, lousicidal, and/or pediculicidal activity.

In some embodiments, the pediculicidal composition comprises an activating solvent system at a concentration preferably from about 2% to about 85% by weight, preferably between about 2% to about 55% by weight, more preferably from between about 2% to about 35% by weight. A particularly preferred activating solvent system, in some embodiments, is a combination of an alcohol and hydrocarbon, and in more specific embodiments, a preferred alcohol is selected from phenoxyethanol and benzyl alcohol, and a preferred hydrocarbon is mineral oil. In some embodiments the alcohol is benzyl alcohol and the hydrocarbon is mineral oil.

The term "solvent" as used herein refers to a liquid that is capable of dissolving the metal chelating agent. In some embodiments, the preferred solvent includes, but is not limited to: alcohols, heterocyclic compounds, alkoxylated alcohol, esters, thio compounds, hydrocarbons, fats and oils.

In some further embodiments, the preferred solvents include, but are not limited to: ethanol, octyldodecanol, benzyl alcohol, phenoxyethanol, methyl pyrrolidone, polyethylene glycol 300, PPG-15 stearyl ether, diisopropyl adipate, propylene glycol caprylate, propylene glycol dicaprylate, isopropyl myristate, dimethyl sulfoxide, limonene, caprylic/capric triglyceride and peanut oil.

In yet further embodiments, the preferred solvent is a mixture of solvents selected from the group consisting of ethanol, octyldodecanol, benzyl alcohol, phenoxyethanol, methyl pyrrolidone, polyethylene glycol 300, PPG-15 stearyl ether, diisopropyl adipate, propylene glycol caprylate, propylene glycol dicaprylate, isopropyl myristate, dimethyl sulfoxide, limonene, caprylic/capric triglyceride and peanut oil.

In some embodiments, the preferred solvent is an alcohol. In a further embodiment, the solvent is ethanol, octyldodecanol, benzyl alcohol or phenoxyethanol, preferably benzyl alcohol. In yet a further embodiment the solvent is a mixture of ethanol, octyldodecanol, benzyl alcohol or phenoxyethanol.

In some embodiments, the pediculicidal composition comprises a solvent at a concentration from about 0.5% to about 35% by weight, preferably from about 0.5% to about 10% by weight.

The term "co-solvent" as used herein refers to a liquid that is miscible with the solvent. In some embodiments, the preferred co-solvent is a hydrocarbon or ester. In a further embodiment, the co-solvent is mineral oil or caprylic/capric triglycerides, preferably mineral oil.

In some embodiments, the preferred pediculicidal composition comprises a co-solvent at a concentration from about 2% to about 50% by weight, preferably from about 2% to about 35% by weight.

The solvent and co-solvent can be mixed with the metal chelating agent in any order. For example, in some embodiments, the metal chelating agent is dissolved by the solvent, followed by addition of the co-solvent. In other embodiments the metal chelating agent is dissolved in the co-solvent, followed by the addition of the solvent. In yet other embodiments, the metal chelating agent is dissolved by a mixture of the solvent and co-solvent, or by the solvent and co-solvent being added to the metal chelating agent at about the same time.

The term "carrier vehicle" as used herein refers to a solution, an emulsion, a gel, an ointment, a spray, a foam or a mixture thereof that may comprise water, the activating solvent system, and at least one agent selected from the group consisting of a thickening agent, a pH adjuster, one or more emulsifying agents, and an anti-oxidant, an emulsifier and an emulsion stabilizer or a mixture thereof. In some embodiments, the carrier vehicle may be a clear, single-phase liquid, a water-in-oil emulsion, an oil-in-water emulsion, a mixed emulsion, a lotion, a cream, an aqueous gel, a non-aqueous gel, a hydrophobic ointment, a hydrophilic ointment, an aerosol spray, a non-aerosol spray, an aerosol foam, a non-aerosol foam or a mixture thereof. In a further embodiment, the carrier vehicle is an aqueous gel or lotion comprising water, an activating solvent system and at least one agent selected from the group consisting of a thickening agent, a pH adjuster, one or more emulsifying agents and an anti-oxidant, or a mixture thereof.

In some embodiments, the pediculicidal composition comprises a carrier vehicle having water at a concentration of about 15% to about 98% by weight, preferably from about 35% to about 95% by weight.

The term "thickening agent" as used herein refers to a substance that is capable of changing the viscosity of the carrier vehicle. In some embodiments, the preferred thickening agent includes, but is not limited to: agar, acrylic acid polymers and copolymers, alginates and salts and derivatives thereof, carrageenan, chitosan, cellulose derivatives, dextrin, gelatin, gum, gum derivatives, maltodextrin, pectin, polycarbophil, polydextrose, polyethylene glycol (PEG), polyethylene oxide, poly(methyl vinyl ether/maleic anhydride) and copolymers and derivatives thereof, polyvinyl alcohol, polyvinylpyrrolidone (PVP), pregelatinized starch, hyaluronan, sulfobutylether beta-cyclodextrin or mixtures thereof.

In further embodiments, the preferred thickening agent includes, but is not limited to: agar, acritamers, carbomers, pemulens (amine salt, ammonium salt, sodium salt, potassium salt of these polymers), propylene glycol alginate, kappa (sodium salt), iota (sodium salt), lambda, chitosan, hydroxyethyl cellulose, hydroxyethyl methylcellulose, hydroxypropyl cellulose, hydroxypropyl methylcellulose, methylcellulose, sodium carboxymethylcellulose, dextrin, gelatin, acacia, *ceratonia*, guar, tragacanth, xanthan gum, hydroxypropyl guar, guar hydroxypropyltrimonium chloride, maltodextrin, pectin, polycarbophil, polydextrose, PEG 200, PEG 300, PEG 400, PEG 540, PEG 600, PEG 900, PEG 1000, PEG 1450, PEG 1500, PEG 1540, PEG 2000, PEG 3000, PEG 3350, PEG 4000, PEG 4600, PEG 6000, PEG 8000, PEG 20000, PEG 35000, polyethylene oxide, poly(methyl vinyl ether/maleic anhydride) and copolymers and derivatives thereof, polyvinyl alcohol, PVP K12, PVP K15, PVP K17, PVP K25, PVP K30, PVP K60, PVP K90, PVP K120, pregelatinized starch, hyaluronic acid, sodium hyaluronate, sulfobutylether beta-cyclodextrin, trehalose or mixtures thereof.

In yet another embodiment, the preferred thickening agent includes, but is not limited to: propylene glycol alginate, cellulose derivatives, acrylic acid polymers and copolymers or mixtures thereof. In yet another embodiment, the preferred thickening agent includes, but is not limited to: propylene glycol alginate, hydroxyethyl cellulose, hydroxyethyl methylcellulose, hydroxypropyl cellulose, hydroxypropyl methylcellulose, methylcellulose, sodium carboxymethylcellulose, acritamers, carbomers, pemulens or mixtures thereof. In some embodiments, the thickening agent is carbomer.

In some embodiments, the preferred pediculicidal composition comprises a thickening agent at a concentration from about 0.01% to about 2% by weight, preferably from about 0.1% to about 1% by weight. In some embodiments, more than one thickening agent is used.

The term "emulsifying agent" as used herein refers to a substance that acts as an emulsifier, an emulsion stabilizer or a surfactant. The term "emulsifier" as used herein refers to a substance that aids the dispersion of one liquid in another liquid. In some embodiments, the preferred emulsifier includes, but is not limited to: glycerine, gum, laurate esters, lecithin, polyoxyethylene ether, polyoxyethylene diols, polyvinyl carboxy polymer, polyol, triyglycerol ester, stearic acid, sorbitan stearate or mixtures thereof. In some embodiments, the emulsifier is polyoxyl-40 stearate.

In some embodiments, the preferred pediculicidal composition comprises an emulsifier at a concentration from about 0.1% to about 5% by weight, preferably from about 1% to about 5% by weight. In some embodiments, more than one emulsifier may be used.

The term "emulsion stabilizer" as used herein refers to a substance that aids in the stabilisation of an emulsion. In some embodiments, the preferred emulsion stabilizer includes, but is not limited to: an alcohol, acetic acid, carbomer, gum palmitic acid, polyethylene glycol, isostearic acid, stearic acid, or mixtures thereof.

In some embodiments, the preferred emulsion stabilizer is an alcohol. In a further embodiment, the preferred emulsion stabilizer is cetyl alcohol, stearyl alcohol or a mixture thereof.

In some embodiments, the preferred pediculicidal composition comprises an emulsion stabilizer at a concentration from about 0.1% to about 10% by weight, preferably from about 1% to about 6% by weight.

The term "surfactant" as used herein refers to an agent that lowers the surface tension between two liquids, for example between an aqueous solution and an oil. In some embodiments, the surfactant comprises a non-ionic surfactant, an anionic surfactant, a cationic surfactant or a mixture thereof. In further embodiments, the surfactant includes, but is not limited to: sodium docusate, sodium lauryl sulphate, sodium laureth sulphate, benzethonium chloride, cetrimide, cetylpyridinium chloride ethoxylated carboxylic acids such as PEG-8 stearate, PEG-12 stearate, PEG-20 stearate, PEG-30 stearate, PEG-40 stearate, PEG-50 stearate, PEG-100 stearate, PEG-12 distearate, PEG-32 distearate, PEG-150 distearate and PEG-10 oleate; ethoxylated glycerides such as PEG-35 castor oil, PEG-40 hydrogenated castor oil and PEG-60 hydrogenated castor oil; polyhydric alcohol esters and ethers, such as methyl gluceth-20 sesquistearate; ethoxylated sorbitan esters such as polysorbate 20, polysorbate 40, polysorbate 60 and polysorbate 80; ethoxylated alcohols such as ceteareth-6, ceteareth-12, ceteareth-20, ceteareth-25, ceteth-10, ceteth-20, laureth-4, laureth-5, laureth-9, laureth-10, laureth-12, laureth-15, laureth-20, laureth-23, oleth-10, oleth-20, steareth-10, steareth-20 and steareth-100; ethoxylated lanolin such as PEG-20 lanolin, PEG-30 lanolin, PEG-75 lanolin, PEG-100 lanolin and PEG-150 lanolin; ethoxylated polysiloxanes such as dimethicone copolyol; propoxylated POE ethers such as poloxamer 124, poloxamer 188, poloxamer 237, poloxamer 338 and poloxamer 407; and alkylpolyglucosides such as caprylyl glucoside, decyl glucoside, lauryl glucoside, coco-glucoside, cetearyl glucoside and isostearyl glucoside or mixtures thereof.

In some embodiments, the surfactant comprises alkylpolyglucoside. In a further embodiment, the surfactant includes, but is not limited to: caprylyl glucoside, decyl polyglucoside, lauryl glucoside, coco-glucoside, cetearyl glucoside and isostearyl glucoside or mixtures thereof. In yet a further embodiment, the surfactant comprises decyl polyglucoside.

In some embodiments, the surfactant is an ethoxylated alcohol. In a further embodiment the surfactant includes, but is not limited to: ceteareth-6, ceteareth-12, ceteareth-20, ceteareth-25, ceteth-10, ceteth-20, laureth-4, laureth-5, laureth-9, laureth-10, laureth-12, laureth-15, laureth-20, laureth-23, sodium laureth sulphate oleth-10, oleth-20, steareth-10, steareth-20, steareth-100 or mixtures thereof. In yet a further embodiment the surfactant comprises sodium laureth sulphate.

In some embodiments, the surfactant comprises an ethoxylated sorbitan ester. In a further embodiment the surfactant includes, but is not limited to: polysorbate 20, polysorbate 40, polysorbate 60, polysorbate 80 or mixtures thereof. In yet a further embodiment, the surfactant comprises polysorbate 20. In some embodiments, the surfactant also acts as an emulsifier. For example, polysorbate 20 acts as a surfactant and an emulsifier. In some embodiments, more than one surfactant is used.

In some embodiments, the pediculicidal composition comprises a surfactant at a concentration from about 0.1% to about 10% by weight, preferably between 0.1% to about 5% by weight. In specific embodiments, a particularly preferred composition comprises polysorbate 20, preferably at a concentration of about 1% to about 5% (w/w), a concentration of about 1% and less than 5%, and more preferably at a concentration of about 1% w/w. Some of the illustrative embodiments provided in the Examples demonstrate an unexpected effect relating to compositions that comprise about 1% w/w of surfactant. These effects may be beneficially observed with the combination of the surfactant with the activating solvent system; however is should be noted that a benefit may be seen with just the activating solvent system alone, or just the surfactant alone, although a composition comprising both components is preferred.

The term "pH adjuster" as used herein refers to a substance that is capable of raising or lowering pH levels. In some embodiments, the pH adjuster comprises a base. In a further embodiment, the pH adjuster includes, but is not limited to: bicarbonates, carbonates, amines, alkanolamines, hydroxides, alkaline earth metal hydroxides, transition metal hydroxides or a mixture thereof. In yet a further embodiment, the pH adjuster includes, but is not limited to: potassium hydroxide or sodium hydroxide. In another embodiment, the pH adjuster comprises triethanolamine. In some embodiments, the pH adjuster can also be a surfactant, for example triethanolamine acts as a pH adjuster and a surfactant.

In some embodiments, the pH adjuster comprises an acid, an acid salt, or a mixture thereof.

In some embodiments, the pH adjuster comprises a buffer. In a further embodiment the buffer includes, but is not limited to: a citrate/citric acid, acetate/acetic acid, phosphate/phosphoric acid, formate/formic acid, propionate/propionic acid, lactate/lactic acid, carbonate/carbonic acid, ammonium/ammonia, edentate/edetic acid, or mixtures thereof.

In some embodiments, the preferred pediculicidal composition comprises a pH adjuster in an amount sufficient to adjust the pH of the composition to a pH of between about 3 to about 9, preferably in an amount sufficient to adjust the pH of the composition to a pH of between about 5 to about 9, more preferably in an amount sufficient to adjust the pH of the composition to a pH of between about 5 to about 7.5.

In some embodiments, the preferred pediculicidal composition comprises a pH adjuster at a concentration from about 0.1% to about 5% by weight, preferably from about 0.1% to about 2% by weight. In some embodiments, more than one pH adjuster is used.

The term "anti-oxidant" as used herein refers to an agent that prevents the oxidative degradation of, or preserves, the other ingredients of the pediculicidal composition. The antioxidant may comprise, or may be selected from the group consisting of, amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, lycopene) and their derivatives, chlorogenic acid and derivatives thereof, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine), typically in very low tolerated doses (e.g. pmol to μmol/kg), and also chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, ethylenediaminetetraacetic acid (EDTA), ethylene glycol tetraacetic acid (EGTA) and their derivatives, unsaturated fatty acids and their derivatives (e.g. γ-linolenic acid, linoleic acid, oleic acid), folic acid and its derivatives, ubiquinone and ubiquinol and derivatives thereof, vitamin C and its derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, α-glucosylnitin, ferulic acid, furfurylideneglucitol, carnosine, butylhydroxytoluene (BHT), butylhydroxyanisole (BHA), nordihydroguaiacic acid, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), vitamin A, vitamin B2, vitamin B6, vitamin B9 (folic acid), vitamin B12, vitamin C, vitamin E, selenium, carotenes (β-carotene, lutein, zeaxanthin, and lycopene), zinc, copper, proanthocyanidins (e.g. anthocyanidins, flavonols [e.g. catechins, epicatechins, procyanidins], flavanones, flavonols), nac n-acetylcysteine, α-lipoic acid, coenzyme Q10, Ginkgo biloba, green tea extract, isothiocyanates (e.g. sulforaphane), phenols (e.g. caffeic acid, and ferulic acid), olive oil, sulfides/thiols (e.g. diallyl sulfide, allyl methyl trisulfide, and dithiolthiones), lycopenes, and the derivatives (salts, esters, ethers, sugars, nucleotides, nucleosides, peptides and lipids) of said active ingredients.

In certain embodiments, the antioxidant may be selected from an antioxidant that is used in, or is approved for use in, pharmaceutical formulations. In some embodiments, the antioxidant may be selected from an antioxidant that is used, or is approved for use in a topical formulation. In the above embodiments, the antioxidant can be included up to, and including, the maximum allowable concentration that is approved for pharmaceutical applications and uses (e.g., topical application/use). In some embodiments the antioxidant can comprise, or be selected from the group consisting of, ascorbic acid, ascorbyl palmitate, BHA, BHT, EDTA, olive oil, propyl gallate, sodium metabisulfite, sodium metabisulfite, sodium sulfite, and tocopherol.

In some embodiments, the antioxidant is selected from BHA, BHT, or a mixture thereof. In further embodiments, the antioxidant is BHT.

The total amount of antioxidants (one or more compounds) in the compositions, when present, can be in an amount of from about 0.001 wt. % to about 30 wt. %, or from about 0.05 wt. % to about 20 wt. %, or about 1 wt. % to about 10 wt. %. The concentration of the antioxidant may be determined by one of skill in the art, and can vary in relatively broad ranges such as, for example, about 0.001 wt. % to about 10%, such as about 0.001 wt. % to about 5 wt. %, or about 0.001 wt. % to about 3 wt. %, or about 0.001 wt. % to about 1 wt. % or about 0.001 wt. % to about 0.1 wt. %, or about 0.001 wt. % to about 0.01 wt. %.

In another non-limiting embodiment, a pediculicidal composition that comprises BHT as an antioxidant, the BHT may be present at a concentration ranging between about 0.001 wt. % to about 10%, such as about 1 wt. % to about 10 wt. % or about 1 wt. % to about 5 wt. %, or about 1 wt. % to about 3 wt. %, or about 2 wt. %. In some embodiments, more than one antioxidant may be used.

The compounds of the invention may be in the form of pharmaceutically, veterinary or agriculturally acceptable salts.

A number of metal chelating agents and other compounds mentioned useful in the present invention can be obtained commercially from specialty chemical companies. Those not commercially available can be synthesized from commercially available starting materials using reactions known to those skilled in the art.

Another aspect of the invention is providing a method of treating a human head lice infestation comprising administering to a subject in need thereof, a therapeutically effective amount of a pediculicidal composition substantially as described herein below.

In some embodiments, a pediculicidal composition according to the present invention may be applied to the hair or skin of a subject in need thereof. The pediculicidal composition may be applied topically in the form of a solution, cream, emulsion, lotion, gel, spray, ointment or foam. In some embodiments, the composition can be prepared as a medicament for preventing or treating lice infestation. As discussed herein, embodiments provide for the use of the disclosed composition in a medicament that comprises one or more other active agents that may have ovicidal (kills eggs), lousicidal (kills lice), or pediculicidal (kills both eggs and lice) activity or efficacy.

To the extent that the disclosure relates to treatment with certain compositions, it should be understood that the disclosure also particularly contemplates use of the compositions described herein for the treatment of a pest infestation on a host. Also contemplated are uses in the topical treatment of a lice infestation on a host. In some of the above embodiments, the use of the composition kills lice. In some of the above embodiments, the use of the composition inhibits egg hatching. In some of the above embodiments, the use of the composition kills lice and inhibits egg hatching. In these embodiments, the composition on the host kills more lice when compared to a vehicle composition that does not include 5,5'-dimethyl-2,2'-dipyridyl, but otherwise includes the same components.

The terms "administering" and "administration" are used herein to mean any method which delivers the composition to a subject in such a manner as to provide the desired ovicidal, lousicidal or pediculicidal activity or efficacy. In some embodiments the administering comprises contacting the subject (e.g., topical application) with the composition. In some embodiments the administering comprises contacting or application of the composition to the skin, hair, or both skin and hair of the subject.

The term "pediculicidal efficacy" is used herein to refer to the ability of a composition with a metal chelating agent to treat a lice infestation and thus be effective in preventing lice eggs from hatching and effective to kill lice.

The terms "effective amount," "an amount effective to," or a "therapeutically effective amount" are used herein to refer to an amount of the pediculicidal composition sufficient to provide treatment or prevention of lice infestation in a human, or otherwise control an infestation. The effective amount of a pediculicidal composition may vary depending on the host and the type and level of infestation. In one embodiment, the pediculicidal composition is applied to the scalp or into the hair of a person suffering from head lice infestation and is left on the treated person for a period of time. Preferably the period of time is about 10 minutes. In embodiments the period of time is from about 10 minutes to about 120 minutes, about 10 minutes to about 60 minutes, about 10 minutes to about 50 minutes, about 10 minutes to about 40 minutes, about 10 minutes to about 30 minutes, or about 10 minutes to about 20 minutes. In a further embodiment, the pediculicidal composition is washed off the hair or scalp of a person with warm or cold water.

In another embodiment, the pediculicidal composition may be used as part of a regimen for the treatment of a disease, disorder or condition of the skin. The pediculicidal composition may be used in combination with a separate pharmaceutical dosage form. In some embodiments for example, the pediculicidal composition of the invention may be used in combination with another lousicidal or ovicidal composition. Such compositions are known to those of skill in the art may include compositions such as compositions containing permethrin, malathion, ivermectin, spinosad or phenothrin and/or in combination with non-chemical head lice and nits treatments or the use of wet combing.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

The invention will hereinafter be described by way of the following non-limiting Examples.

EXAMPLES

Example 1. Manufacture of a Pediculicidal Composition (0.74% w/w Formulation of Table 1)

5,5'-dimethyl-2,2'-dipyridyl, benzyl alcohol (solvent), light mineral oil (co-solvent), Polysorbate 20 (surfactant) and BHT (anti-oxidant) are added to a vessel, heated to 55±2° C. and mixed using a propeller mixer until completely dissolved. The clear solution is cooled to 35° C. or less under propeller mixer. Carbopol 980 (thickening agent) is added and mixed until completely dispersed. The mixture is transferred into a tank.

Purified water is added to the original vessel, stirred, transferred to the tank and mixed until homogenous using the propeller mixer. Trolamine is added and mixed until homogenous using the propeller mixer. The pH of the solution is measured while mixing, adjusted with additional trolamine to reach a pH of 6.5-7.5 and then mixed for a total of 60 minutes, after which time the pH is verified and adjusted to pH 6.5-7.5 with additional trolamine, if required.

TABLE 1

Formulation of 0.74% w/w 5,5'-dimethyl-2,2'-dipyridyl lotion

| Material | Quantity % w/w | Quantity (kg) | Function |
|---|---|---|---|
| Oil phase | | | |
| 5,5'-dimethyl 2,2'-dipyridyl | 0.74 | 0.296 | Active ingredient |
| Light mineral oil | 24.00 | 9.6 | co-solvent |
| Benzyl Alcohol | 2.00 | 0.8 | solvent |

TABLE 1-continued

Formulation of 0.74% w/w 5,5'-dimethyl-2,2'-dipyridyl lotion

| Material | Quantity % w/w | Quantity (kg) | Function |
|---|---|---|---|
| Polysorbate 20 | 1.00 | 0.4 | surfactant |
| Butylated hydroxytoluene | 0.50 | 0.2 | anti-oxidant |
| Total oil phase | 28.24 | 11.296 | |
| Aqueous phase | | | |
| Purified water USP | 71.41 | 28.564 | |
| Carbopol 980 | 0.15 | 0.06 | Thickening agent |
| Trolamine | 0.20 | 0.08 | pH adjuster/ surfactant |
| Trolamine | QS | | pH adjuster |
| Total aqueous phase | 71.76 | 28.784 | |
| Total | 100.00 | 40.00 | |

Example 2. Manufacture of a Pediculicidal Composition (0.74% Formulation of Table 6 and Table 7)

Oil phase: 5,5'-dimethyl-2,2'-dipyridyl, benzyl alcohol (solvent), mineral oil (co-solvent), and polysorbate 20 (surfactant) are added to a vessel and are mixed until a clear solution is obtained. The mixture can be heated to 50-60° C. to facilitate the dissolution of the components. The clear solution is cooled to below 30° C.

Water phase: Purified water is added to a separate vessel and stirred. While stirring, carbomer (thickening agent) is added slowly. The stirring is continued until the carbomer is fully hydrated.

Emulsification: The water phase is stirred and the oil phase is added to the water phase. Stirring is continued to ensure the oil phase is uniformly dispersed in the water phase. Stirring is continued and trolamine is added. The mixture is stirred until homogenous. The pH of the mixture is in the range from 6.7 to 7.3.

Example 3. Effect of Formulated 5,5'-Dimethyl-2,2'-Dipyridyl on Egg Hatching in *Pediculus humanus capitis*

Gravid female lice were permitted to lay eggs over a 24 hour period. The eggs were counted, inspected under a light microscope and all eggs that appeared undamaged were allocated to one of two treatment groups. One group of 10 eggs was exposed to 5,5'-dimethyl-2,2'-dipyridyl in a formulation (52-06-01), while the second group of 10 eggs was exposed to the formulation only (vehicle, 52-06-02) Table 2. The two formulations were as follows:

TABLE 2

| Component | 52-06-01 | 52-06-02 |
|---|---|---|
| 5,5'-dimethyl-2,2'-dipyridyl | 0.38% | 0.00% |
| Octyldodecanol | 11.9% | 12.0% |
| Capric/Caprylic Triglycerides | 37.7% | 38.0% |
| Sodium Lauryl Ether Sulphate (70%) | 6.0% | 6.0% |
| Cetyl Alcohol | 1.2% | 1.2% |
| Stearyl Alcohol | 1.2% | 1.2% |
| Glyceryl Monostearate | 1.2% | 1.2% |
| PEG-40 Stearate | 2.4% | 2.4% |
| Water | 36.8% | 36.7% |

TABLE 2-continued

| Component | 52-06-01 | 52-06-02 |
|---|---|---|
| Benzyl Alcohol | 0.99% | 1.0% |
| Butylated Hydroxy Toluene | 0.098% | 0.099% |
| Potassium Dihydrogen phosphate | 0.050% | 0.050% |
| Dipotassium Hydrogen phosphate | 0.15% | 0.15% |

The protocol was as follows:
Treatments:
Following a 10 minute exposure to either the 52-06-01 or 56-06-02 formulations the eggs were subsequently washed for 1 minute with water (~37° C.) before being placed at 31° C. in a humid incubator and monitored over time for signs of development specifically of the eyes and through to subsequent hatching.
Results:
The results (summarised in Table 3) indicate that a 0.37% w/w formulation of 5,5'-dimethyl-2,2'-dipyridyl can significantly suppress egg hatching in head lice. Out of a total of ten eggs treated with the formulation containing 5,5'-dimethyl-2,2'-dipyridyl, two of the eggs developed, but only one of these eggs hatched. Overall, 90% of the eggs in the treatment arm failed to hatch. In the vehicle treated group, only one egg failed to develop, of the remaining eggs, 60% of the eggs actually hatched, and 30% developed into nymphs but did not hatch. This data shows that a formulation containing 5,5'-dimethyl-2,2'-dipyridyl with an activating solvent system and surfactant can significantly inhibit head lice eggs from hatching compared to vehicle.

TABLE 3

| Treatment | 5,5'-dimethyl-2,2'-dipyridyl | Vehicle |
|---|---|---|
| Day 1 of observation | | |
| Stage of development | 1 eye development 9 no eye development | 0 eye development |
| Day 4 | | |
| Stage of development | 1 hatched 1 eye development 8 no eye development | 4 eye development 6 no eye development |
| Day 5 | | |
| Stage of development | 1 hatched 1 eye development 8 no eye development | 8 eye development 2 no eye development |
| Day 6 | | |
| Stage of development | 1 hatched 1 eye development 8 no eye development | 9 eye development 1 no eye development |
| Day 7 | | |
| Stage of development | 1 hatched 1 eye development 8 no eye development | 5 hatched 4 eye development 1 no eye development |
| Day 12 | | |
| Stage of development | 1 hatched 1 eye development 8 no eye development | 6 hatched 3 eye development 1 no eye development |

Example 4. Evaluation of Pediculicidal Efficacy of Compositions Against *Pediculus humanus humanus*

TABLE 4

| | 5,5'-dimethyl-2,2'-dipyridyl compositions | | | | | |
|---|---|---|---|---|---|---|
| Component (Function) | 07-08-04 Quantity (% w/w) | 11-08-14 Quantity (% w/w) | 11-08-13 Quantity (% w/w) | 27-08-02 Quantity (% w/w) | 26-08-10 Quantity (% w/w) | 26-08-04 Quantity (% w/w) |
| 5,5'-dimethyl-2,2'-dipyridyl (Metal chelating agent) | 0.37 | 0.37 | 0.37 | 0.55 | 0.74 | 0.00 |
| Octyldodecanol (Solvent/co-solvent) | 12.00 | 12.00 | — | — | — | — |
| Caprylic/capric Triglycerides (solvent/co-solvent) | 17.50 | 17.50 | — | — | — | — |
| Mineral Oil (Co-solvent) | — | — | 5.00 | 5.00 | 5.00 | 5.00 |
| Cetyl Alcohol (Emulsion Stabilizer) | 2.40 | — | — | — | — | — |
| Stearyl Alcohol (Emulsion Stabilizer) | 2.40 | — | — | — | — | — |
| Carbomer 1342 (Thickening agent) | — | 1.00 | — | — | — | — |
| Carbomer (Thickening agent) | — | — | 0.30 | 0.30 | 0.30 | 0.30 |
| Triethanolamine (pH Adjuster) | — | 1.10 | 0.35 | 0.35 | 0.35 | 0.35 |
| Glyceryl Monostearate (Emulsifier) | 2.40 | — | — | — | — | — |
| Polyoxyl-40 Stearate (Emulsifier) | 4.80 | — | — | — | — | — |
| Benzyl Alcohol (Solvent/preservative) | 1.00 | 5.00 | 2.00 | 2.00 | 2.00 | 2.00 |
| Sodium laureth sulfate-70% (surfactant) | 6.00 | 6.00 | — | — | — | — |
| Polysorbate 20 (surfactant) | — | — | 1.00 | 1.00 | 1.00 | 1.00 |
| Monobasic Potassium Phosphate (pH Adjuster) | 0.04 | — | — | — | — | — |

TABLE 4-continued

| | 5,5'-dimethyl-2,2'-dipyridyl compositions | | | | | |
|---|---|---|---|---|---|---|
| Component (Function) | 07-08-04 Quantity (% w/w) | 11-08-14 Quantity (% w/w) | 11-08-13 Quantity (% w/w) | 27-08-02 Quantity (% w/w) | 26-08-10 Quantity (% w/w) | 26-08-04 Quantity (% w/w) |
| Dibasic Potassium Phosphate (pH Adjuster) | 0.16 | — | — | — | — | — |
| Purified Water (Aqueous solvent) | 50.93 | 57.03 | 90.98 | 90.80 | 90.61 | 91.35 |
| Total | 100.00 | 100.00 | 100.00 | 100.00 | 100.00 | 100.00 |

The above formulations (Table 4) were prepared and assessed for pediculicidal efficacy. Each composition comprises 5,5'-dimethyl-2,2'-dipyridyl and the carrier vehicle comprising a solvent system containing a solvent and a co-solvent, water and other ingredients such as one or more emulsifying agents, a thickening agent and pH adjuster which together are formulated as a lotion, cream, foam or a gel. The pediculicidal efficacy was determined by measuring the ovicidal activity (Eggs/% Hatch), and the lousicidal activity (Lice/% Mortality) of each composition. A low percentage, such as between 0% and about 10% of lice eggs hatching, indicates that a composition has good ovicidal activity. A high percentage of dead lice, such as between about 85% and 100% mortality, indicates that a composition has good lousicidal activity. The compositions that exhibit good ovicidal activity and good lousicidal activity are pediculicidal compositions. The results of the pediculicidal efficacy study are shown in Table 5.

TABLE 5

Efficacy of 5,5'-dimethyl-2,2'-dipyridyl compositions as ovicides (Eggs/% Hatch) and lousicides (Lice/% Mortality)

| Product | Eggs/% Hatch | Lice/% Mortality (17 hrs) |
|---|---|---|
| 0.37% w/w 5,5'-dimethyl-2,2'-dipyridyl lotion Formula 07-08-04 | 2 | 1 |
| 0.9% w/w 5,5'-dimethyl-2,2'-dipyridyl lotion Formula 48-06-01 | Not determined | 25 |
| 0.37% w/w 5,5'-dimethyl-2,2'-dipyridyl lotion Formula 11-08-14 | 0 | 11 |
| 0.37% w/w 5,5'-dimethyl-2,2'-dipyridyl lotion Formula 11-08-13 | 0 | 46 |
| 0.54% w/w 5,5'-dimethyl-2,2'-dipyridyl lotion Formula 27-08-02 | Not determined | 99 |
| 0.74% w/w 5,5'-dimethyl-2,2'-dipyridyl lotion Formula 26-08-10 | Not determined | 100 |
| 0% (Vehicle) 5,5'-dimethyl-2,2'-dipyridyl lotion Formula 26-08-04 | Not determined | 15 |

The results demonstrate that 5,5'-dimethyl-2,2'-dipyridyl formulation is a good ovicide when it is in a lotion (Formula 07-08-04) (Formula 11-08-14 and Formula 11-08-13) composition at a concentration of 0.37% w/w. However, the lousicidal activity at this concentration of 5,5'-dimethyl-2,2'-dipyridyl is poor in a solvent system that comprises octyldodecanol and caprylic/capric triglycerides. Significantly improved lousicidal activity is seen at the same concentration of 5,5'-dimethyl-2,2'-dipyridyl (0.37% w/w) when the solvent system comprises benzyl alcohol and mineral oil (e.g., see Formula 11-08-13). This activity is further improved by increasing the concentration of 5,5'-dimethyl-2,2'-dipyridyl to 0.54% w/w; (Formula 27-08-02) and 0.74% w/w; (Formula 26-08-10) while maintaining the solvent system comprising benzyl alcohol and mineral oil. A similar vehicle lotion composition (i.e., 0.0% 5,5'-dimethyl-2,2'-dipyridyl composition—Formula 26-08-04) did not demonstrate any significant lousicidal activity, indicating that the solvent system per se is not contributing significantly to the efficacy of the pediculicidal compositions. The 5,5'-dimethyl-2,2'-dipyridyl lotion compositions exhibit lousicidal activity when the solvent system comprises benzyl alcohol, as the solvent, and mineral oil, as the co-solvent. The results also show that the 5,5'-dimethyl-2,2'-dipyridyl lotion compositions of Formula 27-08-02 and Formula 26-08-10 that contain both mineral oil and benzyl alcohol in the solvent system exhibit lousicidal activity. The solvent system appears to activate the lousicidal activity of 5,5'-dimethyl-2,2'-dipyridyl in the lotion compositions possibly through enhancing uptake of the compound by the target parasite and it can therefore be considered as an activating solvent system.

Example 5. Evaluating Pediculicidal Compositions Against *Pediculus humanus humanus*

In the development of an effective formulation to kill lice a number of formulations were tested, by varying the composition of the activating solvent system and other ingredients of the carrier vehicle. The results are provided in Table 6. Increasing the percentage of the surfactant polysorbate 20 from 1% (32-08-02) to 5% (32-08-10) resulted in a dramatic decrease in the lousicidal activity of 5,5'-dimethyl-2,2'-dipyridyl. This is in contrast to the teachings of U.S. Pat. No. 5,858,383, which suggests use of high concentrations of surfactants such as polysorbate 20 (10%) or triethanolamine (14.5%) for topical compositions for ectoparasite treatments in which an air impermeable composition is used for suffocating lice. Those treatments required that the compositions of the U.S. Pat. No. 5,858,383 patent must be applied to the host for more than four hours, preferably 8 hours. Moreover, those formulations had little or no effect on the eggs as the formulations were considered to be acting through a suffocation method on the crawling stage of the lice lifecycle. In contrast, the compositions of the current invention have a rapid (about 10 minutes) pharmacological effect due to the actions of the metal chelating agent, 5,5'-dimethyl-2,2'-dipyridyl. Moreover, the compositions of the present invention are effective against both the lice and the eggs. Furthermore, the composition and the concentration of the surfactant in the invention described here is shown to be important in the formulation insofar as it enhances the efficacy of the active compound, 5,5'-dimethyl-2,2'-dipyridyl against the lice and eggs, rather than the surfactant alone having a lice killing effect per se. This is supported by poor activity of the vehicle formulations.

The results further demonstrate that changing the surfactant from 1% polysorbate 20 to 1% sodium laureth sulphate resulted in a loss of lousicidal activity. It was also discovered that when additional solvents were evaluated there was a significant impact on the lousicidal activity. For example formulations containing no surfactant and different solvent systems, such as 5% Diisopropyl Adipate (02-09-09) or 5% Capric/capylic Triglyceride (02-09-10) and 5% Propylene Glycol Caprylate (13-09-14) were less active than the benzyl alcohol/mineral oil solvent system with surfactant (35-08-03), which is consistent with the results obtained in Example 4

TABLE 6

Assessment of the effects of varying components on lousicidal activity against *Pediculus humanus humanus*.

| Formulation code | Components | Lousicidal Efficacy/ % Mortality |
|---|---|---|
| 32-08-02 | 1% Polysorbate 20<br>1% Phenoxyethanol<br>20% MO<br>0.74% 5,5'-dimethyl-2,2'-dipyridyl | 96 |
| 35-08-10 | 5% Polysorbate 20<br>1% Phenoxyethanol<br>20% MO<br>0.74% 5,5'-dimethyl-2,2'-dipyridyl | 5 |
| 35-08-03 | 1% Polysorbate 20<br>2% BA<br>5% MO<br>0.55% 5,5'-dimethyl-2,2'-dipyridyl | 100 |
| 35-08-11 | 5% Polysorbate 20<br>2% BA<br>5% MO<br>0.55% 5,5'-dimethyl-2,2'-dipyridyl | 10 |
| 02-09-07 | 1% sodium laureth sulphate<br>1% Phenoxyethanol<br>20% MO<br>0.74% 5,5'-dimethyl-2,2'-dipyridyl | 32 |
| 02-09-09 | 5% Diisopropyl Adipate<br>1% Phenoxyethanol<br>20% MO<br>0.74% 5,5'-dimethyl-2,2'-dipyridyl | 13 |
| 02-09-10 | 5% Capric/capylic Triglyceride<br>1% Phenoxyethanol<br>20% MO<br>0.74% 5,5'-dimethyl-2,2'-dipyridyl | 31 |
| 13-09-14 | 5% Propylene Glycol Caprylate<br>2% BA<br>5% MO<br>0.55% 5,5'-dimethyl-2,2'-dipyridyl | 10 |

"BA" = benzyl alcohol
"MO" = mineral oil

These results clearly demonstrate the major effect that changing surfactant percentage and composition had on lousicidal activity. This data supported the decision for a low surfactant concentration (1%) of polysorbate 20 in the preferred formulation. In addition, the above data also support the advantages of the benzyl alcohol/mineral oil combination as an activating solvent system to enhance the activity of 5,5'-dimethyl-2,2'-dipyridyl.

Example 6. Evaluation of Lousicidal Efficacy of Compositions Against *Pediculus humanus humanus*

TABLE 7

0.74% w/w and 0% (Vehicle) 5,5'-dimethyl-2,2'-dipyridyl compositions and lice efficacy data.

| Component | 0.74% w/w 5,5'-dimethyl-2,2'-dipyridyl 17-09-27 Quantity (% w/w) | 0% (Vehicle) 5,5'-dimethyl-2,2'-dipyridyl 17-09-13 Quantity (% w/w) | Function |
|---|---|---|---|
| 5,5'-dimethyl-2,2'-dipyridyl | 0.74 | — | Metal chelating agent |
| Benzyl Alcohol | 2.00 | 2.00 | Solvent/Preservative |
| Mineral Oil | 24.00 | 24.00 | Co-solvent |
| Carbomer | 0.20 | 0.20 | Thickening agent |
| Trolamine | 0.25 | 0.25 | pH Adjuster/surfactant |
| Polysorbate 20 | 1.00 | 1.00 | surfactant |
| Purified Water | 71.81 | 72.55 | Carrier/Aqueous solvent |
| Total | 100.00 | 100.00 | |
| Lousicidal Efficacy/ % Mortality | 100% | 30% | |

Table 7 shows the results of a study comparing the mortality rate of a formulation containing the metal chelating agent and an activating solvent system to a formulation where the metal chelating agent is absent. The 0.74% formulation of 5,5'-dimethyl-2,2'-dipyridyl results in a 100% mortality rate, indicating that the composition has excellent lousicidal activity. This is in contrast to the vehicle treated group, where there was low (30%) lousicidal efficacy. This data is consistent with the previous examples which indicate that the composition and concentration of the carrier vehicle ingredients, notably the activating solvent system and surfactant compositions and concentrations, are important to optimise the efficacy of the active ingredient, 5,5'-dimethyl-2,2'-dipyridyl.

This formulation including 0.5% BHT was also evaluated for its ovicidal activity. See Table 8.

TABLE 8

Evaluation of in vitro ovicidal efficacy of compositions against *Pediculus humanus humanus* comparing 0.74% w/w 5,5'-dimethyl-2,2'-dipyridyl and 0% (Vehicle).

| Component | 0.74% w/w 5,5'-dimethyl-2,2'-dipyridyl 17-09-37 Quantity | 0% (Vehicle) 5,5'-dimethyl-2,2'-dipyridyl 17-09-35 Quantity |
|---|---|---|
| 5,5'-dimethyl-2,2'-dipyridyl | 0.74 | — |
| Mineral Oil | 24.00 | 24.00 |
| Carbomer | 0.20 | 0.20 |
| Trolamine | 0.2 | 0.2 |
| Benzyl Alcohol | 2.00 | 2.00 |
| Polysorbate 20 | 1.00 | 1.00 |
| Butylated Hydroxy Toluene | 0.50 | 0.50 |
| Purified Water | 71.36 | 72.1 |
| Total | 100.00 | 100.00 |
| Ovicidal Efficacy/ % egg hatch | 0 | 65% |

The results shown in Table 8 indicate that 5,5'-dimethyl-2,2'-dipyridyl produces significant ovicidal activity compared to the vehicle formulation which is ineffective in preventing egg hatch. The lousicidal and ovicidal activity of this formulation support that it is a highly effective pediculicide, and further reinforce the beneficial effects of the activating solvent system in enhancing the activity of 5,5'-dimethyl-2,2'-dipyridyl.

Example 7. Evaluation of Ex Vivo Ovicidal Efficacy of 5,5'-Dimethyl-2,2'-Dipyridyl (Abametapir) Against *Pediculus humanus capitis*

The following formulation was used in the ex vivo study (Table 9)

TABLE 9

| Component | 0.74% w/w 5,5'-dimethyl-2,2'-dipyridyl Quantity | 0% (Vehicle) 5,5'-dimethyl-2,2'-dipyridyl Quantity |
|---|---|---|
| 5,5'-dimethyl-2,2'-dipyridyl | 0.74 | — |
| Mineral Oil | 24.00 | 24.00 |
| Carbomer | 0.15 | 0.15 |
| Trolamine | 0.2 | 0.2 |
| Benzyl Alcohol | 2.00 | 2.00 |
| Polysorbate 20 | 1.00 | 1.00 |
| Butylated Hydroxy Toluene | 0.50 | 0.50 |
| Purified Water | 71.41 | 72.15 |
| Total | 100.00 | 100.00 |

In this study the formulation as listed in Table 9 containing 0.74% 5,5'-dimethyl-2,2'-dipyridyl, (abametapir), was evaluated in a double-blind, vehicle-controlled randomized clinical trial. The primary aim of the trial was to evaluate the ovicidal efficacy of a single application of abametapir lotion 0.74% w/w intended for the treatment of head lice. The primary end point was the proportion of hatched eggs pre-treatment relative to proportion of hatched eggs post-treatment for the formulation containing abametapir and vehicle treated eggs following a 14 day incubation.

This ex vivo study involved identifying subjects with an active head lice infestation (active being defined as the presence of at least 3 live lice and at least 10 undamaged eggs). A minimum of 5 undamaged eggs were collected both pre and post treatment and their predicted viability assessed under a dissecting microscope before being incubated in a temperature and humidity controlled incubator (30° C. and 60% RH) for 14 days to provide adequate time for the eggs to hatch. After 14 days eggs were assessed as either hatched, unhatched, or partially hatched. Results are presented in Table 10.

TABLE 10

| | 0.74% Abametapir lotion N = 25 | Vehicle Lotion N = 25 |
|---|---|---|
| Egg hatch Pre-treatment | 93.3% (111/119 eggs) | 79.5% (93/117 eggs) |
| Egg hatch Post-treatment | 0% (130/130 eggs)* | 36% (49/136 eggs) |
| Total absolute reduction in hatch rate (CI 95%) | 92.9% | 42.3% |
| The treatment difference | 50.6% | p < 0.0001 |

*Data demonstrates 100% ovicidal efficacy

Table 10 contains data demonstrating a highly significant reduction in the number of eggs that hatched in the 0.74% abametapir treated eggs compared to the vehicle lotion. Abametapir reduced the hatch rate from 93.3% to 0% as compared to vehicle which reduced the hatch rate from 79.5% to 36.0%. This data clearly demonstrates that 100% of all eggs treated with abametapir failed to hatch. Using a generalized estimating equation model to account for the correlation of eggs within subject, the absolute reduction in hatch rate for the abametapir arm was 92.9% (with a 95% confidence interval of 86.5 to 99.4) compared to an absolute reduction of 42.3% (95% confidence interval of 30.2 to 54.4) for the vehicle arm. The treatment difference in the absolute reduction of hatch rates (abametapir minus Vehicle) was 50.6% (p-value<0.0001, with a 95% confidence interval of 36.9 to 64.3).

Example 8. In Vivo Efficacy of 5,5'-Dimethyl-2,2'-Dipyridyl in Treating a Head Lice *Pediculus humanus Capitis* Infestation One hundred and forty two (142) pediatric and adult subjects, three (3) years of age or older, with an active head lice infestation were enrolled in the study. This study assessed the efficacy of a single application of 2 different dose levels (0.37% w/w and 0.74% w/w of 5,5'-dimethyl-2,2'-dipyridyl) compared to a vehicle control. The formulations were prepared as described in Table 9. Subjects were treated for 10 minutes with a lotion containing one of two dose levels of 5,5'-dimethyl-2,2'-dipyridyl or the vehicle lotion. After 10 minutes the lotion was rinsed out of the subjects hair with water and towel dried. At day 1, 7 and 14 post treatment the hair was examined for the presence of live lice. If any live lice were detected on any of the three visits the subject was deemed a treatment failure. The primary endpoint to the study was that proportion of subjects who were lice free at day 14. Results from this study indicated that both concentrations of 5,5'-dimethyl-2,2'-dipyridyl demonstrated statistically significant and clinically relevant treatment success compared to the vehicle control group. The primary efficacy results showed that 67.4% of subjects in the 0.37% treatment group and 85.7% of subjects in the 0.74% treatment group had treatment success compared to 23.4% of subjects in the vehicle group (p<0.001). The safety results demonstrated that a single application of 5,5'-dimethyl-2,2'-dipyridyl at two dose levels 0.37% w/w and 0.74% w/w was safe and well tolerated.

Example 9. In Vivo Efficacy of 5,5'-Dimethyl-2,2'-Dipyridyl in Treating a Head Lice *Pediculus humanus capitis* Infestation A total of seven hundred and four (704) pediatric and adult subjects, six (6) months of age or older, with an active head lice infestation were enrolled in two separate Phase 3 studies. These studies assessed the efficacy of a single application of 0.74% w/w abametapir compared to a vehicle control (refer Table 9, above). Subjects were treated for 10 minutes with a lotion containing abametapir or the vehicle lotion alone. After 10 minutes the lotion was rinsed out of the subjects hair with water and towel dried. At day 1, 7 and 14 post treatment the hair was examined for the presence of live lice. If any live lice were detected on any of the three visits the subject was deemed a treatment failure. The primary endpoint to the study was that proportion of index subjects (youngest member of the household with at least 3 live lice at the commencement of the study) who were lice free at all follow-up visits through day 14. Results from these studies indicated that 0.74% abametapir lotion demonstrated statistically significant and clinically relevant treatment success compared to the vehicle control group. The primary efficacy results showed that 81.1% (study 1) and 81.8% (study 2) of subjects in the 0.74% treatment group had treatment success compared to 50.9% (study 1) and 47.2% (study 2) of subjects in the vehicle group (p=0.001) study 1and (p<0.001) study 2. The safety results demonstrated that a single application of abametapir 0.74% w/w was safe and well tolerated.

It will be appreciated by persons skilled in the art that numerous variations and/or modifications may be made to the invention as shown in the specified embodiments without departing from the spirit or scope of the invention as broadly described. The present embodiments are, therefore, to be considered in all respects as illustrative and not restrictive.

Any discussion of documents, acts, materials, devices, articles or the like which was included in the present specification is solely for the purpose of providing a context for the present invention. It is not to be taken as an admission that any or all of these matters form part of the prior art base or were common general knowledge in the field relevant to the present invention as it existed in any country before the priority date of each claim of this application.

What is claimed is:

1. A composition comprising:
   5,5'-dimethyl-2,2'-dipyridyl; and
   a carrier vehicle comprising water and an activating solvent system comprising an alcohol and a hydrocarbon;
   wherein the alcohol is benzyl alcohol in an amount from about 0.5% to about 10% by weight and the hydrocarbon is mineral oil in an amount from about 2% to about 35% by weight, and wherein the said alcohol and hydrocarbon act solely as an activating solvent system;
   wherein 5,5'-dimethyl-2,2'-dipyridyl is present in the composition at a concentration from about 0.25% by weight or greater, and wherein said composition exhibits both ovicidal and lousicidal activity.

2. A composition comprising:
   5,5'-dimethyl-2,2'-dipyridyl in an amount from about 0.25% to about 5% by weight;
   and an activating solvent system comprising:
   benzyl alcohol in an amount from about 0.5% to about 10% by weight;
   mineral oil in an amount from about 2% to about 35% by weight;
   water in an amount from about 35% to about 95% by weight;
   an alkyl acrylate crosspolymer in an amount from about 0.1% to about 1% by weight;
   trolamine in an amount from about 0.1% to about 2% by weight;
   butylated hydroxy toluene from about 0.1% to about 1.5% by weight; and
   polysorbate 20 in an amount from about 0.1% to about 5% by weight.

3. The composition of claim 1, wherein said alcohol further comprises an additional aromatic alcohol or an aryl alcohol.

4. The composition of claim 3, wherein said additional aromatic or aryl alcohol comprises phenoxyethanol.

5. The composition of claim 1, wherein 5,5'-dimethyl-2,2'-dipyridyl is present in the composition at a concentration from about 0.25% to about 5% by weight.

6. The composition of claim 1, wherein 5,5'-dimethyl-2,2'-dipyridyl is present in the composition at a concentration from about 0.5% to about 5% by weight.

7. The composition of claim 1, wherein 5,5'-dimethyl-2,2'-dipyridyl is present in the composition at a concentration from about 0.5% to about 1% by weight.

8. The composition of claim 1, wherein said carrier vehicle is a solution, a gel, a cream, an ointment, a foam, a spray or an emulsion.

9. A composition comprising:
   a) 5,5'-dimethyl-2,2'-dipyridyl in an amount from about 0.25% to about 5% by weight;
   b) an activating solvent system comprising:
      i) a solvent at a concentration of from about 0.5% w/w to about 35% w/w, and
      ii) a cosolvent at a concentration of from about 2% w/w to about 50% w/w;
   c) a thickening agent; and
   wherein the 5,5'-dimethyl-2,2'-dipyridyl is solubilized in the activating solvent system and exhibits both ovicidal and lousicidal activity.

10. The composition of claim 9, wherein said thickening agent is selected from the group consisting of acritamers, alkyl acrylate crosspolymer or copolymers of acrylic acid and C10-C30 alkyl acrylate.

11. The composition of claim 9, wherein said thickening agent is selected from the group consisting of: agar, acritamers, alkyl acrylate crosspolymer, copolymers of acrylic acid and C10-C30 alkyl acrylate or an amine salt, ammonium salt, sodium salt, potassium salt thereof, propylene glycol alginate, chitosan, hydroxyethyl cellulose, hydroxyethyl methylcellulose, hydroxypropyl cellulose, hydroxypropyl methylcellulose, methylcellulose, sodium carboxymethylcellulose, dextrin, gelatin, acacia, *ceratonia*, guar, tragacanth, xanthan gum, hydroxypropyl guar, guar hydroxypropyltrimonium chloride, maltodextrin, pectin, polycarbophil, polydextrose, PEG 200, PEG 300, PEG 400, PEG 540, PEG 600, PEG 900, PEG 1000, PEG 1450, PEG 1500, PEG 1540, PEG 2000, PEG 3000, PEG 3350, PEG 4000, PEG 4600, PEG 6000, PEG 8000, PEG 20000, PEG 35000, polyethylene oxide, poly(methyl vinyl ether/maleic anhydride) and copolymers and derivatives thereof, polyvinyl alcohol, PVP K12, PVP K15, PVP K17, PVP K25, PVP K30, PVP K60, PVP K90, PVP K120, pregelatinized starch, hyaluronic acid, sodium hyaluronate, sulfobutylether beta-cyclodextrin, trehalose and mixtures thereof.

12. The composition of claim 9, wherein the thickening agent is present at a concentration of from about 0.01% wt/wt to about 2% wt/wt.

13. The composition of claim 9, wherein said thickening agent is an alkyl acrylate crosspolymer.

* * * * *